United States Patent
Li

(10) Patent No.: US 9,916,661 B2
(45) Date of Patent: Mar. 13, 2018

(54) IMAGE PROCESSING APPARATUS, IMAGE PROCESSING METHOD, AND MAGNETIC RESONANCE IMAGING SYSTEM

(71) Applicant: TOSHIBA MEDICAL SYSTEMS CORPORATION, Otawara-shi (JP)

(72) Inventor: Guang Li, Beijing (CN)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 120 days.

(21) Appl. No.: 15/019,198

(22) Filed: Feb. 9, 2016

(65) Prior Publication Data

US 2016/0239951 A1 Aug. 18, 2016

(30) Foreign Application Priority Data

Feb. 12, 2015 (CN) .......................... 2015 1 0075935
Nov. 16, 2015 (JP) ................................ 2015-224214

(51) Int. Cl.
*G06T 7/00* (2017.01)
*A61B 5/00* (2006.01)
(Continued)

(52) U.S. Cl.
CPC ............ *G06T 7/003* (2013.01); *A61B 5/7271* (2013.01); *G06T 5/006* (2013.01); *G06T 5/50* (2013.01);
(Continued)

(58) Field of Classification Search
CPC ......... G06T 3/0068; G06T 5/006; G06T 5/50; G06T 7/30; G06T 7/337; A61B 5/055;
(Continued)

(56) References Cited

U.S. PATENT DOCUMENTS

2007/0223832 A1* 9/2007 Matsumoto .................... 382/260
2011/0052031 A1* 3/2011 Feiweier et al. ............... 382/131
2015/0146999 A1* 5/2015 Feiweier et al. ...... G06T 11/008
382/275

OTHER PUBLICATIONS

Takahashi et al., "The Basic Discussion of Distortion Effects Caused by Dephase and Eddy Current in Diffusion Weighted Image," Imaging Center of Northern Fukushima Medical Center, retrieval date Aug. 3, 2015, http://tohoku-b.umin.ac.jp/data/17bukaizassi/17_page162.pdf with partial English translation.

(Continued)

*Primary Examiner* — Andrew W Johns
(74) *Attorney, Agent, or Firm* — Nixon & Vanderhye P.C.

(57) ABSTRACT

An image processing apparatus according to an embodiment includes processing circuitry. The processing circuitry selects from a plurality of diffusion-weighted images with different applied directions of a motion probing gradient magnetic field pulse or different diffusion sensitive coefficients, a diffusion-weighted image that conforms to a predetermined condition. The processing circuitry configured to register the selected diffusion-weighted image with a reference image for which the diffusion sensitive coefficient being set to a reference value to correct the selected diffusion-weighted image. The processing circuitry configured to register the corrected diffusion-weighted image with each of the other diffusion-weighted images of the plurality of diffusion-weighted images to correct each of the other diffusion-weighted images.

12 Claims, 7 Drawing Sheets

(51) Int. Cl.
  *G06T 5/00* (2006.01)
  *G06T 5/50* (2006.01)
  *G06T 7/33* (2017.01)

(52) U.S. Cl.
  CPC .... *G06T 7/337* (2017.01); *G06T 2207/10016* (2013.01); *G06T 2207/10092* (2013.01); *G06T 2207/20216* (2013.01)

(58) Field of Classification Search
  CPC .... A61B 5/7207; A61B 5/7221; G01R 33/20; G01R 33/44; G01R 33/56; G01R 33/5602; G01R 33/5608; G01R 33/56509
  See application file for complete search history.

(56) References Cited

OTHER PUBLICATIONS

Rhode et al., "Comprehensive Approach for Correction of Motion and Distortion in Diffusion-Weighted MRI", Magnetic Resonance in Medicine, 51, pp. 103-114, 2004.

\* cited by examiner

IMAGE PROCESSING APPARATUS, IMAGE PROCESSING METHOD, AND MAGNETIC RESONANCE IMAGING SYSTEM

CROSS-REFERENCE TO RELATED APPLICATIONS

This application is based upon and claims the benefit of priority from Chinese Patent Application No. 201510075935.0, filed on Feb. 12, 2015; and Japanese Patent Application No. 2015-224214, filed on Nov. 16, 2015, the entire contents of all of which are incorporated herein by reference.

FIELD

The disclosure generally relates to medical image processing, and more particularly, to a medical image processing apparatus and a medical image processing method for correcting a Diffusion-Weighted Image (DWI) and a magnetic resonance imaging device including the medical image processing apparatus.

BACKGROUND

Diffusion Tensor Imaging (DTI) or Diffusion Tensor Tractography (DTT) is an important approach for function analysis based on a Magnetic Resonance (MR) image. Typically, a Diffusion Tensor Image (DTI) is obtained based on a group of (generally at least six) DWIs corresponding to different gradient directions (directions of applied electromagnetic field).

As a DWI may distort (for example, due to motion, eddy current or the like), it is needed to correct the DWI. Generally, each DWI in a group of DWIs (i.e., DWIs in the same sequence) is corrected by registering the DWI with an diffusion sensitive coefficient b=0 image.

BRIEF DESCRIPTION OF THE DRAWINGS

The invention will be better understood with reference to the following description taken in conjunction with accompanying drawings, in which same or like reference numbers denote same or like components. The accompanying drawings, together with the detailed description below, are incorporated into and form a part of the specification and serve to illustrate, by way of example, preferred embodiments of the disclosure and to explain the principle and advantages of the disclosure. In the drawings.

DETAILED DESCRIPTION

Figure 1:
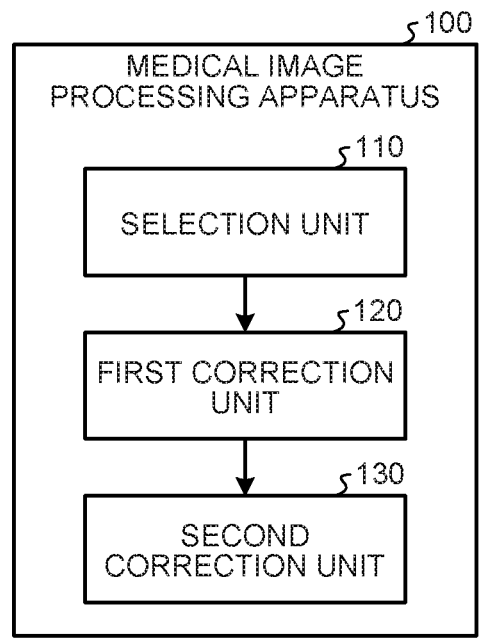
FIG. 1 is a block diagram showing an example of the configuration of a medical image processing apparatus according to an embodiment of the disclosure.

The following presents a brief summary of the disclosure to provide a basic understanding of some aspects of the disclosure. It should be appreciated that the brief summary, which is not the exhaustive overview of the disclosure, is not intended to identify the key or critical parts of the disclosure or limit the scope of the disclosure, but merely to present some concepts in a simplified form as a prelude to the more detailed description that is discussed later.

An image processing apparatus according to an embodiment includes processing circuitry. The processing circuitry selects from a plurality of diffusion-weighted images with different applied directions of a motion probing gradient magnetic field pulse or different diffusion sensitive coefficients, a diffusion-weighted image that conforms to a predetermined condition. The processing circuitry configured to register the selected diffusion-weighted image with a reference image for which the diffusion sensitive coefficient being set to a reference value to correct the selected diffusion-weighted image. The processing circuitry is configured to register the corrected diffusion-weighted image with each of the other diffusion-weighted images of the plurality of diffusion-weighted images to correct each of the other diffusion-weighted images.

In accordance with another aspect of the disclosure, a magnetic resonance imaging device is provided, which includes the above medical image processing apparatus.

In accordance with still another aspect of the disclosure, a medical image processing method is provided, which includes a step of selecting, according to a predetermined quality criterion, at least one image having relatively high quality from a group of diffusion-weighted images as a representative image. The method further comprises a step of correcting the selected representative image by registering the representative image with the diffusion sensitive coefficient b=0 image corresponding to the group of diffusion-weighted images. The method further comprises a step of correcting the other images in the group of diffusion-weighted images by registering the other images with the corrected representative image.

Embodiments of the disclosure are beneficial to improving the accuracy and the processing efficiency of DWI image correction.

Embodiments of the disclosure are described below with reference to accompanying drawings. The elements and features described in an drawing or embodiment of the disclosure can be combined with those shown in one or more other drawings or embodiments. It should be noted that for the sake of clarity, representation and description of the components and processing that are unrelated to the disclosure but well known to those of ordinary skill in the art are omitted in the drawings and description.

As shown in FIG. 1, a medical image processing apparatus 100 according to an embodiment of the disclosure comprises a selection unit 110, a first correction unit 120 and a second correction unit 130. The medical image processing apparatus 100 is given as one example of an image processing apparatus.

The selection unit 110 is configured to select, according to a predetermined quality criterion, at least one image having relatively high quality from a group of Diffusion-weighted images (DWIs) as a representative image. In other words, the selection unit 110 selects from a plurality of diffusion-weighted images with different diffusion sensitive coefficients, a diffusion-weighted image that conforms to a predetermined condition.

In the disclosure, "a group of DWIs" refers to DWIs of the same imaged part which are corresponding to different diffusion sensitive gradients, wherein a diffusion sensitive gradient field parameter is called a diffusion sensitive coefficient or b value. A group of DWIs may be used to generate a DTI.

The selection unit 110 may select a representative image according to various predetermined quality criteria. For example, according to an embodiment, the selection unit may select a representative image according to the distortion degree and/or the structural sharpness of the DWIs. In other words, the selection unit 110 selects the representative image based on the distortion degree and the structural sharpness of each of the plurality of diffusion-weighted images as a predetermined condition. However, the predetermined quality criterion is not limited to this, for example, one or more DWIs in the group of DWIs which have a relatively high similarity with a corresponding b=0 image may be selected as one or more representative images, as will be described later.

The first correction unit 120 is configured to correct the representative image by registering the representative image selected by the selection unit 110 with an image of which the diffusion sensitive coefficient b=0 (hereinafter referred to as "b=0 image") corresponding to the group of diffusion-weighted images. In other words, the first correction unit 120 registers the selected diffusion-weighted image with a reference image for which the diffusion sensitive coefficient is set to a reference value, and corrects the selected diffusion-weighted image. The first correction unit 120, for example, corrects the selected diffusion-weighted image by using an image with the diffusion sensitive coefficient set to zero as the reference image.

Registration-based image correction can be performed in a way known in the art, for example, in the way described in Comprehensive Approach for Correction of Motion and Distortion in Diffusion-Weighted MRI, G. K. Rohde, et al., Magnetic Resonance in Medicine 51:103-114 (2004).

Besides, when there are two or more representative images, each representative image is separately registered with the b=0 image so as to obtain a corresponding corrected representative image.

The second correction unit 130 is configured to correct the other images in the group of diffusion-weighted images by registering the other images with the corrected representative image. In other words, the second correction unit 130 registers the corrected diffusion-weighted image with each of the other diffusion-weighted images of the plurality of diffusion-weighted images to correct each of the other diffusion-weighted images. The second correction unit 130 may use a registration correction method similar to or different from that used by the first correction unit 120.

Besides, when there are two or more representative images, the other images in the group of DWIs can be corrected according to the result of the registration of the other images with each of the corrected representative images, wherein the corrected representative image which is relatively low in registration deviation may be selected as a final registration object for correction, or the other images in the group of DWIs are corrected by comprehensively considering the registration results of the other images with a plurality of corrected representative images. Alternatively, the other images in the group of DWIs except for the representative images can be divided into groups corresponding to each of the representative images respectively, and each group of images are registered with a corresponding corrected representative image so as to be corrected. For example, the grouping may be carried out according to the similarities of the DWIs with the corrected representative images so that the second correction unit can perform registration on images having relatively high similarity.

As stated above, each DWI is corrected by registering the DWI with a b=0 image according to the prior art. However, according to the above described embodiment of the disclosure, a representative image selected from a group of DWIs is corrected by being registered with a b=0 image, and the other images in the group of DWIs are corrected by being registered with the corrected representative image. As the selected representative image has a relatively high image quality, the registration of the selected representative image with the b=0 image is relatively high in accuracy and processing efficiency. Besides, as DWIs are relatively similar to each other in the feature such as grey level distribution, the registration of the other images in the group of DWIs with the corrected representative image is relatively high in accuracy and processing efficiency. Therefore, compared with the prior art, the medical image processing apparatus according to embodiments of the disclosure is capable of correcting a DWI more accurately and more efficiently.

The predetermined quality criterion used by the selection unit to select a representative image may include the distortion degree of the DWI, the structural sharpness of the DWI or the combination thereof. Next, an embodiment of the selection of a representative image by taking structural sharpness as a predetermined quality criterion and an embodiment of the selection of a representative image by taking distortion degree as a predetermined quality criterion are described separately.

Figure 2:
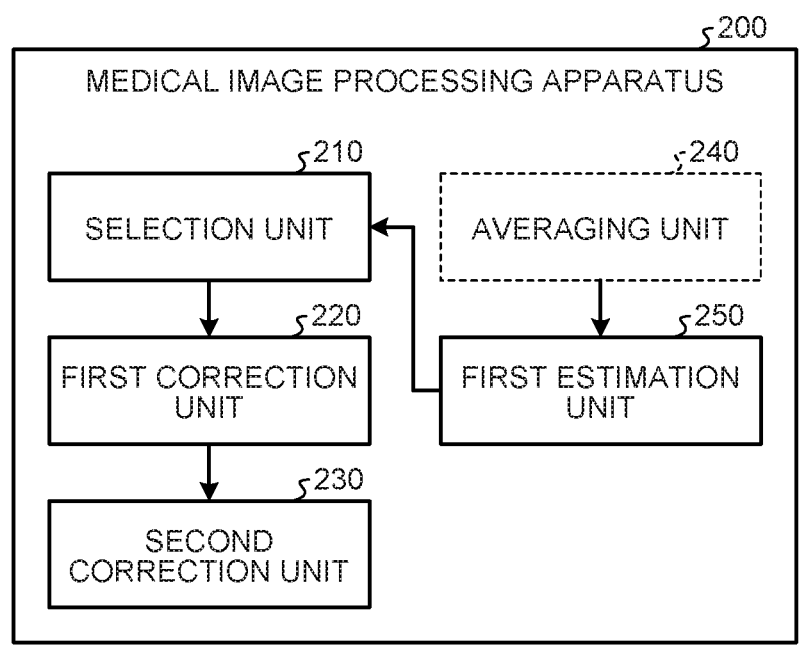
FIG. 2 is a block diagram showing an example of the configuration of a medical image processing apparatus according to another embodiment of the disclosure.

As shown in FIG. 2, a medical image processing apparatus 200 according to an embodiment of the disclosure comprises a selection unit 210, a first correction unit 220, a second correction unit 230, an averaging unit 240 and a first estimation unit 250. The first correction unit 220 and the second correction unit 230 are similar in configuration to corresponding units described above with reference to FIG. 1.

According to the embodiment, the averaging unit 240 and the first estimation unit 250 are configured to estimate the structural sharpness of each DWI, and the selection unit 210 is configured to select a representative image according to the structural sharpness estimated by the first estimation unit 250.

Specifically, the averaging unit 240 is configured to determine the average image of at least part of the group of DWIs. The first estimation unit 250 is configured to estimate the structural sharpness of each DWI according to the DWI and the determined average image.

In a certain DWI, for a reason such as eddy current, the structural information of a certain region may be lost, for example, the contrast of a certain region may be too low to reflect the structural feature in the region. As the loss of structural information may occur in different regions in different DWIs, the effect caused by the information loss in an individual image on the average image may be remedied by the other images. Accordingly, it may be considered that a DWI less different from the average image is relatively high in structural sharpness.

The average image may be determined based on all or part of the group of DWIs. This part of DWIs may be selected randomly or according to a preset criterion. For example, a DWI with a relatively big structural information-lost area is removed through a specific pre-processing (e.g. using a method based on texture or energy gradient) so as to avoid causing a relatively large influence on the average image.

Further, the structural sharpness of a DWI may be estimated based on the DWI and the average image in various ways. According to a specific embodiment, the structural sharpness of a DWI is estimated according to the Sum of Squared Difference (SSD) between the DWI and the average image.

In the foregoing embodiment, the structural sharpness of a DWI is estimated by determining the average image of DWIs and comparing the DWI with the average image. Besides, the image sharpness of a DWI may also be estimated in other ways of image sharpness estimation without introducing an average image.

For example, as shown in FIG. 2, a medical image processing apparatus according to an embodiment may not include an averaging unit. The first estimation unit is configured to estimate the structural sharpness of a DWI according to the local variogram of the DWI. For example, the structural sharpness of a DWI may be estimated by comparing the local variogram of the DWI with that of a b=0 image. Using the b=0 image as a criterion, the structural sharpness of a DWI can be estimated at a relatively high processing efficiency by comparing high-frequency areas of the images based on local variograms.

Besides, other methods of image sharpness estimation known in the art such as a method based on texture and a method based on energy gradient (e.g. refer to: LIU, Xingbao and YUAN, Daocheng "Research on image definition criterion using wavelet transform based on the texture analysis", Chinese Journal of Scientific Instrument, Vol. 8, 2007) may also be used. The structural sharpness of a DWI may also be estimated without comparing the DWI with the average image or the b=0 image, and a representative image is selected based on such evaluation on each DWI.

Next, an embodiment of the selection of a representative image by taking distortion degree as a predetermined quality criterion is described below.

Figure 3:
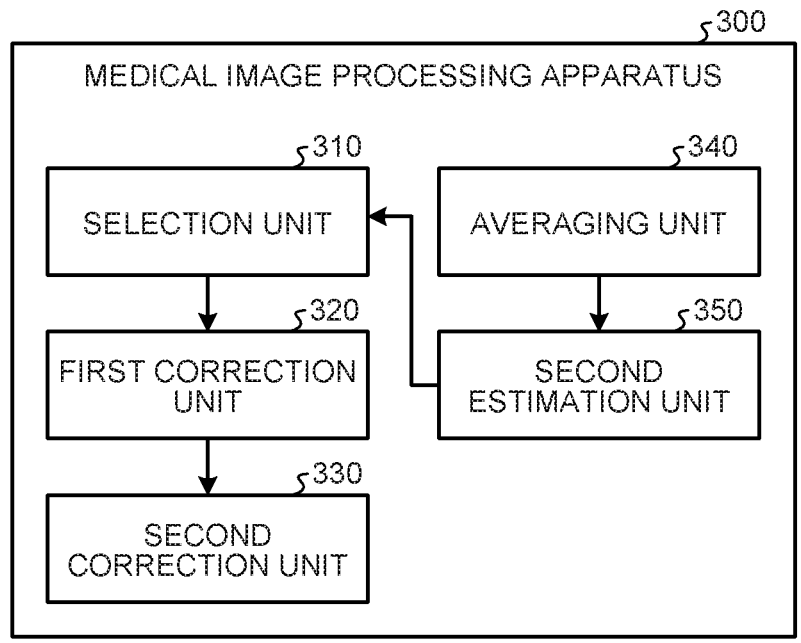
FIG. 3 is a block diagram showing an example of the configuration of a medical image processing apparatus according to still another embodiment of the disclosure.

As shown in FIG. 3, a medical image processing apparatus 300 according to an embodiment comprises a selection unit 310, a first correction unit 320, a second correction unit 330, an averaging unit 340 and a second estimation unit 350. The first correction unit 320 and the second correction unit 330 are similar in configuration to the corresponding units described above. The averaging unit 340 and the second estimation unit 350 are configured to estimate the distortion degree of a DWI, and the selection unit 310 is configured to select a representative image according to the distortion degree estimated by the second estimation unit 350.

Specifically, the averaging unit 340 is configured to determine the average image of at least part of the group of DWIs.

In a certain DWI, distortion may result from, e.g., motion, and the distortion may include, e.g., a translation component and a rotation component. As the influence caused by the distortion in an individual image can be partially remedied by determining an average image, it can be considered that the DWI less different from the average image has relatively low distortion degree.

The second estimation unit 350 is configured to estimate the distortion degree of each DWI according to the DWI and the average image determined by the averaging unit 340.

More specifically, the second estimation unit 350 may be configured to estimate the offset component of the distortion of each DWI according to the difference between the centroid point position of the DWI and that of the average image; moreover, the second estimation unit 350 may be configured to estimate the rotation component of the distortion of the DWI according to the difference between the principle axis angle of the DWI and that of the average image.

Although an embodiment of the selection of a representative image by taking structural sharpness as a predetermined quality criterion and an embodiment of the selection of a representative image by taking distortion degree as a predetermined quality criterion are described above, the predetermined quality criterion for the selection of a representative image is not limited thereto. Next, an embodiment of the selection of a representative image by taking the similarity between a DWI and the b=0 image as a predetermined quality criterion is described with reference to FIG. 4.

Figure 4:
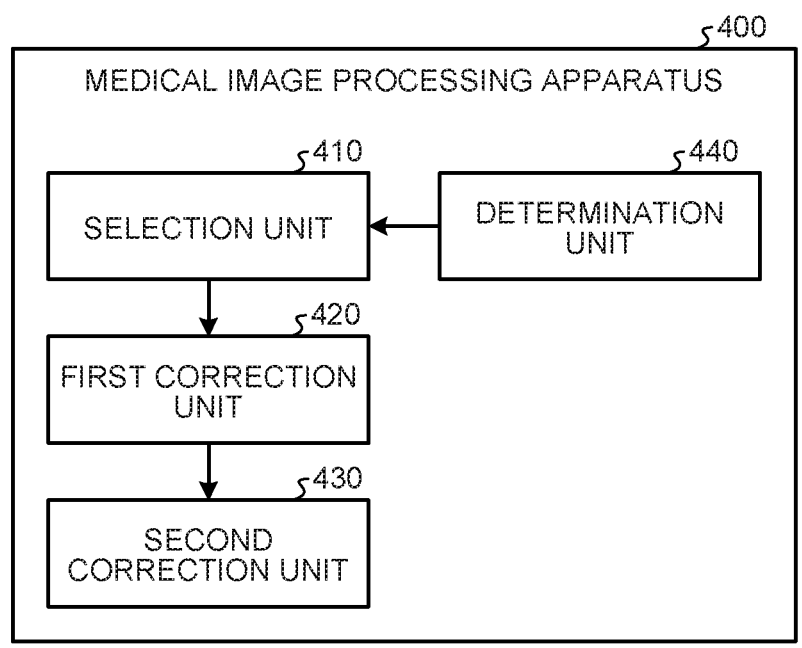
FIG. 4 is a block diagram showing an example of the configuration of a medical image processing apparatus according to yet another embodiment of the disclosure.

As shown in FIG. 4, a medical image processing apparatus 400 according to an embodiment comprises a selection unit 410, a first correction unit 420, a second correction unit 430 and a determination unit 440. The first correction unit 420 and the second correction unit 430 are similar in configuration to the corresponding units described above.

The determination unit 440 is configured to determine the similarity between a DWI and the b=0 image. The selection unit 410 is configured to select a representative image according to the similarity determined by the determination unit 440.

The determination unit 440 can determine the similarity between the DWI and the b=0 image using various image similarity estimation methods known in the art, for example, a method based on grey histogram.

Generally, a DWI relatively similar to the b=0 image is high in structural sharpness and low in distortion degree. Moreover, a relatively accurate correction result can be obtained through the registration of the b=0 image with a relatively similar DWI.

An exemplary embodiment of the selection of a representative image by taking structural sharpness as a predetermined quality criterion, an exemplary embodiment of the selection of a representative image by taking distortion degree as a predetermined quality criterion and an exemplary embodiment of the selection of a representative image by taking the similarity of a DWI with the b=0 image as a predetermined quality criterion are separately described above. A representative image may also be selected according to a combination of the foregoing criteria. For example, an overall image quality estimation may be determined according to the structural sharpness and the distortion degree, and then a representative image is selected according to the overall image quality estimation.

Certain embodiments of a medical image processing apparatus for correcting a DWI are described above, the corrected DWI may be provided by the medical image processing apparatus to another apparatus for a subsequent processing, for example, for the generation of a DTI. In addition, a medical image processing apparatus capable of generating a DTI is also included in the disclosure.

Figure 5:
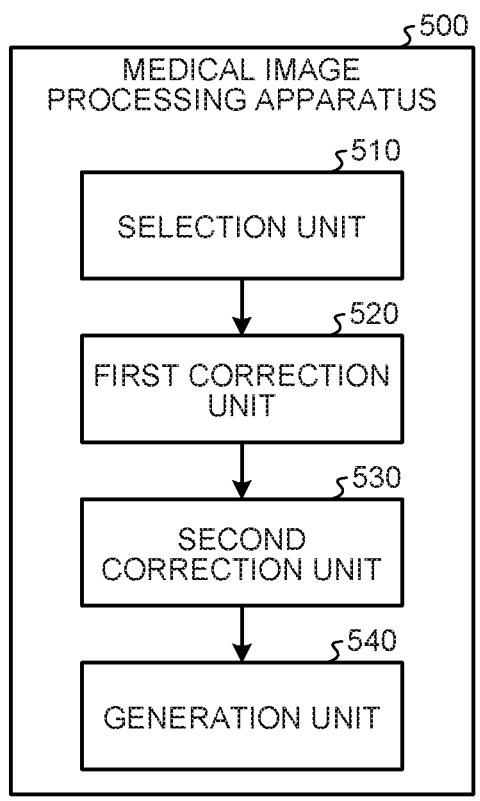
FIG. 5 is a block diagram showing an example of the configuration of a medical image processing apparatus according to yet still another embodiment of the disclosure.

As shown in FIG. 5, a medical image processing apparatus 500 comprises a selection unit 510, a first correction unit 520, a second correction unit 530 and a generation unit 540. The selection unit 510, the first correction unit 520 and the second correction unit 530 can be similar in configuration to corresponding units described above in each embodiment. The generation unit 540 is configured to generate a DTI based on the group of corrected DWIs. The method of generating a DTI based on the group of corrected DWIs is known in the art and is therefore not described here in details.

Figure 6:
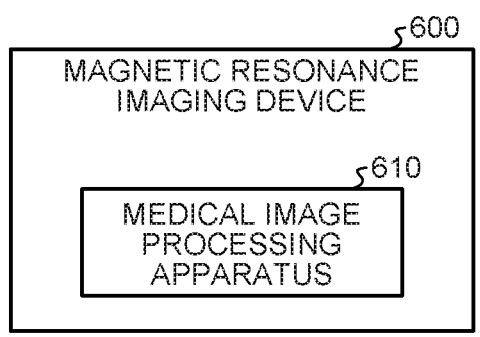
FIG. 6 is a block diagram showing an example of the configuration of a magnetic resonance imaging device according to an embodiment of the disclosure.

Besides, embodiments of the disclosure also include a magnetic resonance imaging device. As shown in FIG. 6, a magnetic resonance imaging device 600 comprises a medical image processing apparatus 610 which may have the configuration described in one of the foregoing embodiments illustrated with reference to FIG. 1-FIG. 5, or any combination thereof.

The above embodiments are given to explain the case in which the selection units 110, 210, 310, 410, and 510 select from a plurality of DWIs with different b values, a diffusion-weighted image that conforms to a predetermined condition. However, the present invention is not limited thereto. For example, the selection units 110, 210, 310, 410, and 510 may select from a plurality of DWIs with different directions of applied pressure of a motion probing gradient (MPG) magnetic field pulse, a diffusion-weighted image that conforms to a predetermined condition. In other words, the selection units 110, 210, 310, 410, and 510 may select from the plurality of diffusion-weighted images with different applied directions of the MPG magnetic field pulse or different diffusion sensitive coefficients (b values), a diffusion-weighted image that conforms to a predetermined condition.

Apparently, some processing or methods are also disclosed when describing the medical image processing apparatus of the above embodiments. These methods are summarized below without repeatedly describing the details which have been discussed above.

Figure 7:
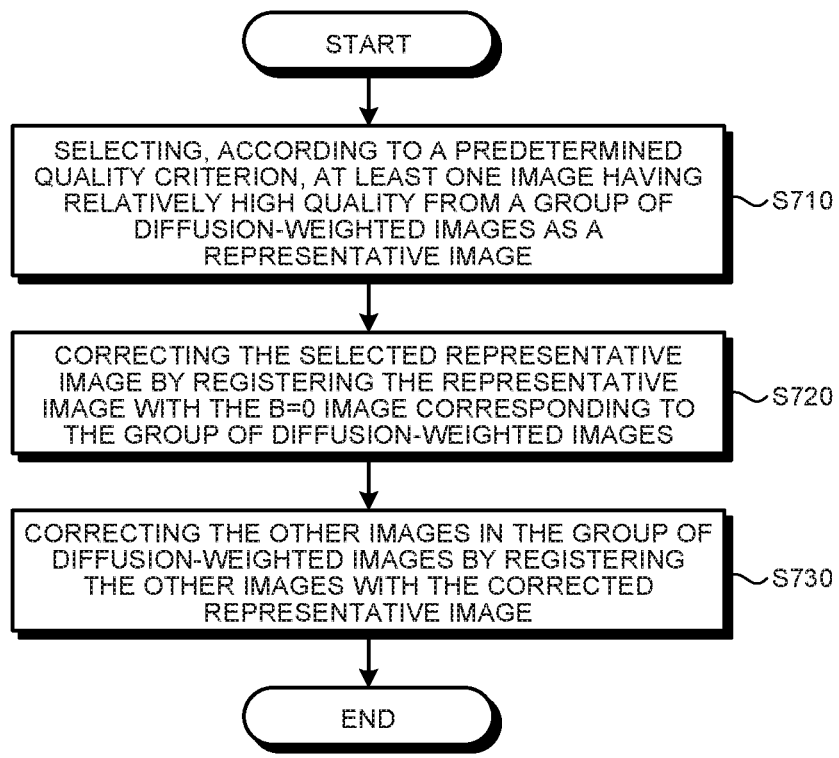
FIG. 7 is a flowchart showing an example of the process of a medical image processing method according to an embodiment of the disclosure.

As shown in FIG. 7, a diffusion-weighted image which conforms to a predetermined condition is selected from the plurality of diffusion-weighted images in step S710 according to a medical image processing method in one embodiment. For example, according to a predetermined quality criterion, at least one image having relatively high quality from a group of DWIs is selected as a representative image.

The representative image may be selected according to various predetermined quality criteria. For example, according to an embodiment, the representative image may be selected according to distortion degree and/or the structural sharpness of the DWIs. Besides, one or more DWIs in the group of DWIs having a relatively high similarity with a corresponding b=0 image may be selected as one or more representative images.

In Step S720, the selected diffusion-weighted image is registered with the reference image to correct the selected diffusion-weighted image. For example, the selected representative image is corrected by registering the representative image with the b=0 image corresponding to the group of DWIs.

As stated above, the representative image may be registered with the b=0 image in various ways.

Besides, when there are two or more representative images, each representative image is registered with the b=0 image to obtain a corresponding corrected representative image.

In Step S730, the corrected diffusion-weighted image is registered with each of the other diffusion-weighted images of the plurality of diffusion-weighted images to correct each of the other diffusion-weighted images. For example, the other images in the group of DWIs are corrected by registering the other images with the corrected representative image.

When there are two or more representative images, the other images in the group of DWIs are corrected according to the result of the registration of the other images with each of the corrected representative images. Alternatively, the images in the groups of DWIs except for the representative images can be divided into groups corresponding to each of the representative images respectively, and each group of images are registered with a corresponding corrected representative image so as to be corrected.

According to the foregoing embodiment of the disclosure, the representative image selected from a group of DWIs is corrected by being registered with a b=0 image, and the other images in the group of DWIs are corrected by being registered with the corrected representative image. Compared with the prior art, the medical image processing apparatus described herein is capable of correcting a DWI more accurately and more efficiently.

For example, distortion correction has been decreased in its accuracy due to reduction in a signal value of a DWI image captured at a high b value, and increase in difference between a b=0 image and the DWI image. However, the medical image processing apparatus according to the embodiments is configured to select a DWI image that is suitable to be registered with the b=0 image. Correction is then made to the DWI image by registering the selected DWI image with the b=0 image, and the corrected DWI image is used to correct the remaining DWI images. As such, the medical image processing apparatus according to the embodiments can accurately perform the distortion correction even with an image with a high b value.

Next, an embodiment of the selection of a representative image by taking structural sharpness as a predetermined quality criterion and an embodiment of the selection of a representative image by taking distortion degree as a predetermined quality criterion are separately described below.

Figure 8:
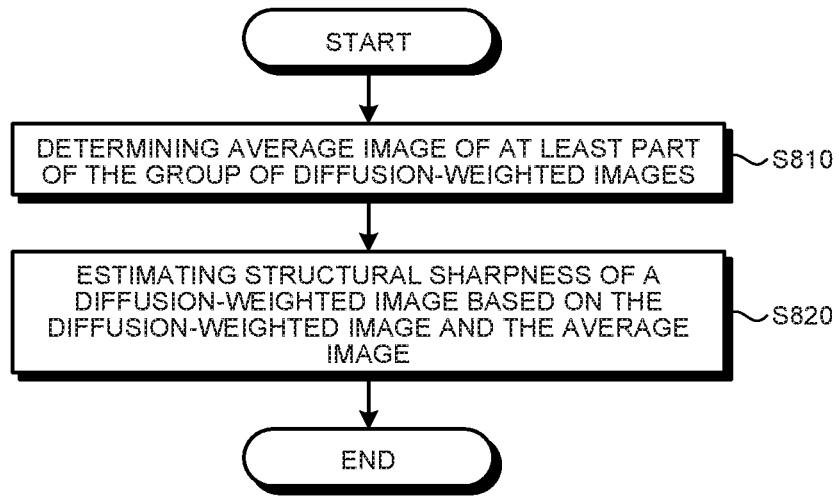
FIG. 8 is a flowchart showing an example of a sub-process of a medical image processing method according to another embodiment of the disclosure.

FIG. 8 schematically exemplifies the process of a representative image selection step included in a medical image processing method according to an embodiment of the disclosure. In this example, a representative image is selected by taking structural sharpness as a predetermined quality criterion.

In Step S810, the average image of at least part of the group of DWIs is determined.

The average image may be determined based on all or part of the group of DWIs. This part of DWIs for determining an average image may be selected randomly or according to a predetermined criterion (e.g. having a relatively small information-lost region).

In Step S820, the structural sharpness of a DWI is estimated based on the DWI and the average image.

As stated above, it may be considered that a DWI less different from the average image has relatively high structural sharpness, and the difference between the DWI and the average image can be measured in various ways.

For example, according to a specific embodiment, the structural sharpness of a DWI is estimated according to the Sum of Squared Difference (SSD) of the DWI and the average image.

In the above embodiment, the structural sharpness of a DWI is estimated by determining the average image of DWIs and comparing the DWI with the average image. Further, the image sharpness of a DWI may also be estimated without introducing an average image.

According to an embodiment, the structural sharpness of a DWI is estimated according to the local variogram of the DWI. For example, the structural sharpness of a DWI is estimated by comparing the local variogram of the DWI with that of a b=0 image.

Furthermore, other image sharpness estimation methods known in the art, for example, the method based on texture and the method based on energy gradient that are mentioned above, are also applicable.

Figure 9:
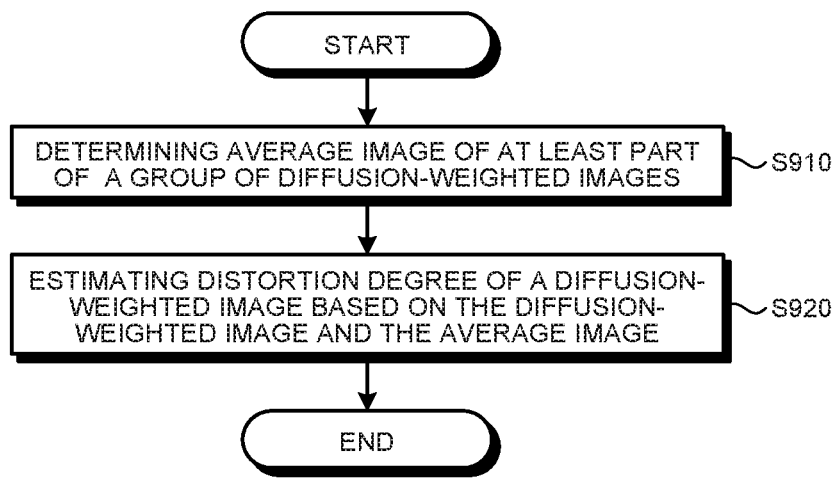
FIG. 9 is a flowchart showing an example of a sub-process of a medical image processing method according to still another embodiment of the disclosure.

FIG. 9 schematically exemplifies the process of a representative image selection step included in a medical image processing method according to another embodiment of the disclosure. In this example, a representative image is selected by taking distortion degree as a predetermined quality criterion.

As shown in FIG. 9, in Step S910, the average image of at least part of a group of DWIs is determined. The average image can be determined in a way similar to that described with reference to FIG. 8.

In Step S920, the distortion degree of a DWI is estimated based on the DWI and the average image.

Figure 10:
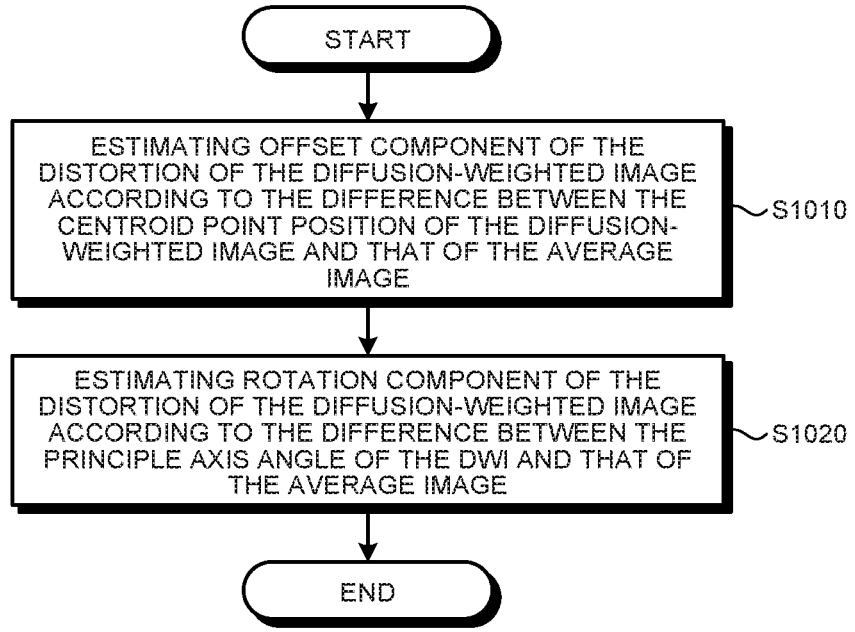
FIG. 10 is a flowchart showing an example of a sub-process of a medical image processing method according to yet another embodiment of the disclosure.

In accordance with a specific embodiment, the process of estimating the distortion degree may include a process of estimating an offset component and a rotation component. FIG. 10 schematically exemplifies a sub-process of estimating the distortion degree of a DWI based on the DWI and the average image.

In Step S1010, the offset component of the distortion of the DWI is estimated according to the difference between the centroid point position of the DWI and that of the average image.

In Step S1020, the rotation component of the distortion of the DWI is estimated according to the difference between the principle axis angle of the DWI and that of the average image.

An embodiment of the selection of a representative image by taking structural sharpness as a predetermined quality criterion and an embodiment of the selection of a representative image by taking distortion degree as a predetermined quality criterion are described above. In accordance with an embodiment, the step of selecting a representative image according to a predetermined quality criterion may include determining the similarity between each DWI and the b=0 image and selecting a representative image according to the determined similarities.

Additionally, a representative image may also be selected according to a combination of the foregoing criteria. For example, an overall image quality estimation may be determined according to the structural sharpness and the distortion degree, and then a representative image is selected according to the overall image quality estimation.

Some embodiments of a medical image processing method for correcting a DWI are described above. In addition, a medical image processing method capable of generating a DTI is also included in the disclosure.

Figure 11:
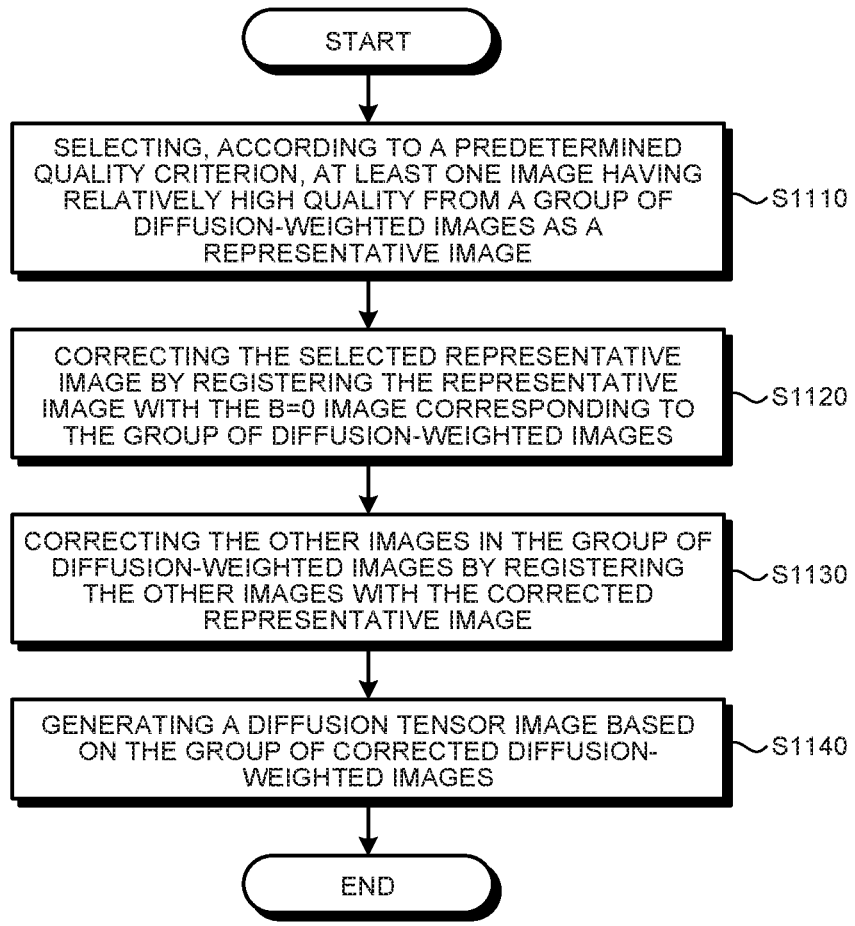
FIG. 11 is a flowchart showing an example of the process of a medical image processing method according to yet another embodiment of the disclosure.

As shown in FIG. 11. in a medical image processing method according to an embodiment, Steps S1110 to S1130 are similar to corresponding steps described above, that is, in Step S1110, at least one image having relatively high quality is selected from a group of DWIs according to a predetermined quality criterion as a representative image; in Step S1120, the selected representative image is corrected by registering the representative image with a b=0 image corresponding to the group of DWI; and in Step S1130, the other images in the group of DWIs are corrected by registering the other images with the corrected representative image.

Further, a medical image processing method according to the embodiment may further comprise a Step S1140 of generating a DTI based on the group of corrected DWIs.

As an example, each step of the foregoing image processing method and each module and/or unit of the foregoing image processing apparatus may be implemented as software, firmware, hardware or a combination thereof. In a case where the steps or modules and/or units are achieved through software or firmware, a program constituting a piece of software (image processing program) for realizing the foregoing method may be installed on a computer having a dedicated hardware structure (e.g. the universal computer 1200 shown in FIG. 12) from a storage medium or network, and the computer, when installed with various programs, is capable of realizing the functions of these programs.

Figure 12:
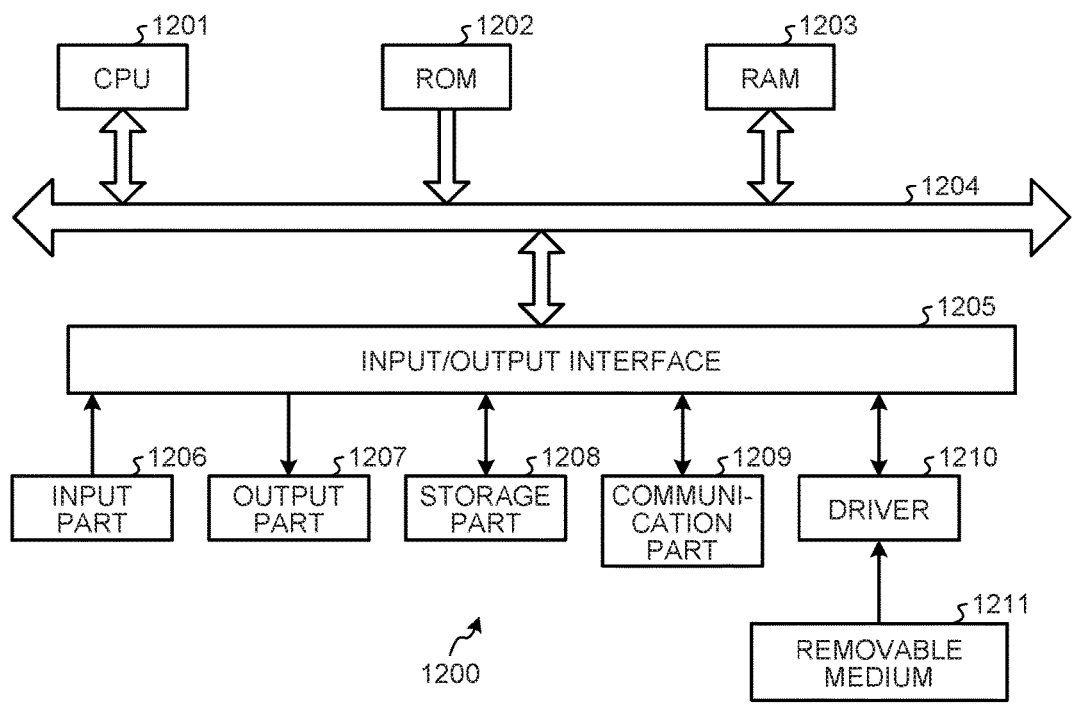
FIG. 12 is a block diagram showing an example of the structure of a computer for realizing the method and the device disclosed herein.

In FIG. 12, a central processing unit (namely, CPU) 1201 executes various processing according to programs stored in a read-only memory (ROM) 1202 or programs loaded to a random access memory (RAM) 1203 from a storage part 1208. The data needed by the CPU 1201 to execute various processing may be stored in the RAM 1203, if needed. The CPU 1201, the ROM 1202 and the RAM 1203 are linked with each other via a bus 1204 with which an input/output interface 1205 is also connected.

The following components are linked with the input/output interface 1205: an input part 1206 (including keyboard, mouse and the like), an output part 1207 (including displays such as cathode ray tube (CRT), liquid crystal display (LCD) and loudspeaker), the storage part 1208 (including hard disk and the like) and a communication part 1209 (including a network interface card such as LAN card and modem). The communication part 1209 executes a communication processing via a network such as the Internet. A driver 1210 may also be linked with the input/output interface 1205, if needed. If needed, a removable medium 1211, for example, a magnetic disc, an optical disc, a magnetic optical disc, a semiconductor memory and the like, may be installed in the driver 1210 to read a computer program therefrom and install the read computer program in the storage part 1208 as required.

In a case where the foregoing series of processing is achieved through software, programs forming the software are installed from a network such as the Internet or a storage medium such as the removable medium 1211.

It should be appreciated by those skilled in the art that the storage medium is not limited to be the removable mediums 1211 shown in FIG. 12 in which programs are stored and which are distributed separated from the apparatus to provide the programs for users. The removable medium 1211 may be, for example, a magnetic disc (including floppy disc (registered trademark)), a compact disc (including compact disc read-only memory (CD-ROM) and digital versatile disk (DVD)), a magnetic optical disc (including mini disc (MD) (registered trademark)), and a semiconductor memory. Alternatively, the storage mediums may be the hard discs included in the ROM 1202 and the storage part 1208, and programs are stored in the storage mediums and can be distributed to users along with the storage medium.

The present invention further provides a program product in which machine-readable instruction codes are stored. The foregoing image processing methods according to the foregoing embodiments of the present invention can be executed when the instruction codes are read and executed by a machine.

Accordingly, a storage medium for carrying the program product in which computer-readable instruction codes are stored is also included in the present invention. The storage medium includes, but is not limited to, a soft disc, an optical disc, a magnetic optical disc, a memory card, a memory stick and the like.

In the foregoing description of specific embodiments of the present invention, the features described and/or shown for an implementation mode may be used in one or more other implementation modes in the same or like way or combined with those of the other implementation modes, or replace those of the other implementation modes.

It should be emphasized that the terms 'comprise/include', as used herein, refer to the presence of a feature, an element, a step or a component, but does not preclude the presence or addition of one or more other features, elements, steps or components.

In the above-described embodiments and examples, each step and/or unit are/is represented with a reference sign consisting of figures. It should be understood by those of ordinary skill in the art that the reference signs are merely intended to facilitate description and drawing but are not to be construed as limiting an order or any other aspect.

The units (processing units) as described in the above embodiments may be integrated into one processing circuitry and may be carried out. The units may be divided in a plurality of processing circuitry and may be carried out.

Furthermore, the methods of the present invention may be implemented sequentially, synchronously or independently according to another time sequence, but not limited to be implemented according to the time sequence described herein. Therefore, the implementation order of the methods described herein is not to be construed as limiting the technical scope of the present invention.

While the present invention has been disclosed with reference to descriptions for the specific embodiments of the present invention, it should be understood that all of the above mentioned embodiments and examples are illustrative instead of limiting. A variety of modifications, improvements or equivalents can be devised by those skilled in the art without departing from the spirit and scope of the claims attached. The modifications, improvements or equivalents should also be considered as being included in the protection scope of the present invention.

What is claimed is:

1. An image processing apparatus comprising processing circuitry configured to:
Select, from a plurality of diffusion-weighted images with different applied directions of a motion probing gradient magnetic field pulse or different diffusion sensitive coefficients, a diffusion-weighted image based on a predetermined condition which includes structural sharpness or similarity between each of the plurality of diffusion-weighted images and a reference image for which the diffusion sensitive coefficient is set to a reference value;
register the selected diffusion-weighted image with a reference image to correct the selected diffusion-weighted image; and
register the corrected diffusion-weighted image with each of the other diffusion-weighted images of the plurality of diffusion-weighted images to correct each of the other diffusion-weighted images.

2. The image processing apparatus according to claim 1, wherein the processing circuitry is configured to correct the selected diffusion-weighted image by using an image with the diffusion sensitive coefficient set to zero as the reference image.

3. The image processing apparatus according to claim 2, wherein the processing circuitry is further configured to estimate structural sharpness of each diffusion-weighted image according to local variogram of each of the plurality of diffusion-weighted images.

4. The image processing apparatus according to claim 2, wherein the processing circuitry is further configured to
determine an average image of at least some of the diffusion-weighted images among the plurality of diffusion-weighted images; and
estimate distortion degree of each diffusion-weighted image according to each of the plurality of diffusion-weighted images and the average image.

5. The image processing apparatus according to claim 4, wherein the processing circuitry is configured to
estimate an offset component of the distortion degree of each diffusion-weighted image according to the difference between a position of centroid point of each of the plurality of diffusion-weighted images and that of the average image; and
estimate a rotation component of the distortion degree of each diffusion-weighted image according to the difference between an angle of a principle axis of each of the plurality of diffusion-weighted images and that of the average image.

6. The image processing apparatus according to claim 1, wherein the processing circuitry selects the diffusion-weighted image based on distortion degree and the structural sharpness for each of the plurality of diffusion-weighted images as the predetermined condition.

7. The image processing apparatus according to claim 6, wherein the processing circuitry is further configured to
determine an average image of at least some of the diffusion-weighted images among the plurality of diffusion-weighted images; and
estimate the structural sharpness of each diffusion-weighted image according to each of the plurality of diffusion-weighted images and the average image.

8. The image processing apparatus according to claim 7, wherein the processing circuitry estimates the structural sharpness of each diffusion-weighted image according to sum of squared difference between each diffusion-weighted image and the average image.

9. The image processing apparatus according to claim 1, wherein the processing circuitry is further configured to determine the similarity and select the diffusion-weighted image according to the similarity as the predetermined condition.

10. An image processing apparatus according to claim 1, wherein the processing circuitry is further configured to generate a diffusion tensor image by using the plurality of diffusion-weighted images corrected.

11. A magnetic resonance imaging (MRI) system comprising processing circuitry configured to:
select, from a plurality of diffusion-weighted images with different applied directions of a motion probing gradient magnetic field pulse or different diffusion sensitive coefficients, a diffusion-weighted image based on a predetermined condition which includes structural sharpness or similarity between each of the plurality of diffusion-weighted images and a reference image for which the diffusion sensitive coefficient is set to a reference value;

register the selected diffusion-weighted image with the reference image to correct the selected diffusion-weighted image; and register the corrected diffusion-weighted image with each of the other diffusion-weighted images of the plurality of diffusion-weighted images to correct each of the other diffusion-weighted images.

12. An image processing method comprising:

Selecting, from a plurality of diffusion-weighted image with different applied directions of a motion probing gradient magnetic field pulse or different diffusion sensitive coefficients, a diffusion-weighted image based on a predetermined condition which includes structural sharpness or similarity between each of the plurality of diffusion-weighted images and a reference image for which the diffusion sensitive coefficient is set to a reference value;

registering the selected diffusion-weighted image with the reference image to correct the selected diffusion-weighted image; and registering the corrected diffusion-weighted image with each of the other diffusion-weighted images of the plurality of diffusion-weighted images to correct each of the other diffusion-weighted images.

* * * * *